(12) United States Patent
Williams et al.

(10) Patent No.: US 9,403,164 B2
(45) Date of Patent: Aug. 2, 2016

(54) SPECIMEN COLLECTION APPARATUS

(71) Applicant: Alpha Tec Systems, Inc., Vancouver, WA (US)

(72) Inventors: Richard O Williams, Vancouver, WA (US); Mark R Williams, Vancouver, WA (US); Christopher O Williams, Vancouver, WA (US)

(73) Assignee: Alpha Tec Systems, Inc., Vancouver, WA (US)

( * ) Notice: Subject to any disclaimer, the term of this patent is extended or adjusted under 35 U.S.C. 154(b) by 0 days.

(21) Appl. No.: 14/660,109

(22) Filed: Mar. 17, 2015

(65) Prior Publication Data

US 2015/0182421 A1    Jul. 2, 2015

Related U.S. Application Data

(62) Division of application No. 13/839,221, filed on Mar. 15, 2013, now Pat. No. 9,138,747.

(60) Provisional application No. 61/615,671, filed on Mar. 26, 2012.

(51) Int. Cl.
*A61B 10/00* (2006.01)
*B01L 3/00* (2006.01)
(Continued)

(52) U.S. Cl.
CPC ............ *B01L 3/502* (2013.01); *A61B 10/0045* (2013.01); *A61J 1/05* (2013.01); *A61J 1/1412* (2013.01); *B01L 3/508* (2013.01); *B01L 9/00* (2013.01); *B65D 43/02* (2013.01); *B65D 53/00* (2013.01); *B65D 81/32* (2013.01); *G01N 1/10* (2013.01); *A61B 10/0051* (2013.01); *A61B 10/0096* (2013.01); *B01L 2200/025* (2013.01); *B01L 2200/0689* (2013.01); *B01L 2200/18* (2013.01);
(Continued)

(58) Field of Classification Search
CPC ..... A61B 10/0045; B01L 3/508; B01L 3/502; B01L 9/00; B01L 2200/0689; B01L 2200/18; B01L 2200/025; B01L 2300/042; B01L 2300/0832
See application file for complete search history.

(56) References Cited

U.S. PATENT DOCUMENTS 3,518,164 A    6/1970    Andelin et al.
3,615,222 A    10/1971   Mead
(Continued)

FOREIGN PATENT DOCUMENTS

EP    0073551    3/1983
WO    9931218    6/1999

OTHER PUBLICATIONS

US Receiving Office, International Search Report for International Application No. PCT/US2013/033582, Jun. 14, 2013, 2 pages.
(Continued)

*Primary Examiner* — Sean Dougherty
(74) *Attorney, Agent, or Firm* — Kolisch Hartwell, P.C.

(57) ABSTRACT

A specimen collection apparatus is provided. The specimen collection apparatus may include a container, a funnel for removable insertion in an opening of the container, a funnel cover; a removable seal, and a dispensing apparatus sealed within the funnel cover in a reagent-specific atmosphere. The dispensing apparatus may include a cap, a reagent housing attached to the cap, and a reagent designed to liquefy a specimen, stabilize the pH of the liquefied specimen, and be compatible with diagnostic procedures.

7 Claims, 9 Drawing Sheets

(51) Int. Cl.
| | |
|---|---|
| *B01L 9/00* | (2006.01) |
| *A61J 1/05* | (2006.01) |
| *A61J 1/14* | (2006.01) |
| *B65D 43/02* | (2006.01) |
| *B65D 53/00* | (2006.01) |
| *B65D 81/32* | (2006.01) |
| *G01N 1/10* | (2006.01) |

(52) U.S. Cl.
 CPC .... *B01L 2300/042* (2013.01); *B01L 2300/0832* (2013.01)

(56) References Cited

U.S. PATENT DOCUMENTS

| | | | |
|---|---|---|---|
| 3,878,571 A | | 4/1975 | Seeley |
| 4,064,760 A | | 12/1977 | Benjamin |
| 4,109,530 A | | 8/1978 | Kim |
| 4,283,498 A | | 8/1981 | Schlesinger |
| 4,335,730 A | | 6/1982 | Griffin |
| 4,589,548 A | | 5/1986 | Fay |
| 4,741,346 A | | 5/1988 | Wong et al. |
| 4,761,379 A | | 8/1988 | Williams et al. |
| 4,823,969 A | * | 4/1989 | Caldwell .................. B67C 9/00 215/260 |
| 4,920,975 A | | 5/1990 | Fay |
| 4,932,081 A | | 6/1990 | Burns |
| 4,981,144 A | | 1/1991 | Carels, Jr. |
| 5,069,878 A | | 12/1991 | Ehrenkranz |
| 5,277,873 A | | 1/1994 | Hsei |
| 5,334,538 A | * | 8/1994 | Parker .................. G01N 33/585 422/401 |
| 5,830,344 A | | 11/1998 | Priddy et al. |
| 5,971,140 A | | 10/1999 | Frutin |
| D425,618 S | | 5/2000 | Niermann et al. |
| 6,145,688 A | | 11/2000 | Smith |
| 6,230,884 B1 | | 5/2001 | Coory |
| 6,325,785 B1 | | 12/2001 | Babkes et al. |
| 6,386,358 B1 | | 5/2002 | North et al. |
| 6,524,530 B1 | | 2/2003 | Igarashi et al. |
| 6,679,375 B1 | | 1/2004 | Coory |
| 7,195,766 B2 | | 3/2007 | White |
| 7,387,216 B1 | | 6/2008 | Smith |
| 2004/0170536 A1 | | 9/2004 | Daykin |
| 2005/0142031 A1 | | 6/2005 | Wickstead et al. |
| 2005/0232813 A1 | * | 10/2005 | Karmali ............... A61B 5/1411 422/410 |
| 2008/0293156 A1 | * | 11/2008 | Smith .................... B01L 3/502 436/174 |
| 2009/0011399 A1 | | 1/2009 | Fischer |
| 2009/0139951 A1 | | 6/2009 | Chen |
| 2009/0216213 A1 | | 8/2009 | Muir et al. |
| 2010/0012613 A1 | | 1/2010 | Anson et al. |
| 2011/0212002 A1 | | 9/2011 | Curry et al. |
| 2012/0046574 A1 | | 2/2012 | Skakoon |
| 2012/0308448 A1 | | 12/2012 | Wong |
| 2013/0164738 A1 | * | 6/2013 | Becker .................... B01L 3/502 435/6.1 |
| 2013/0248045 A1 | | 9/2013 | Williams et al. |

OTHER PUBLICATIONS

US Receiving Office, Written Opinion of the International Searching Authority for International Application No. PCT/US2013/033582, Jun. 14, 2013, 11 pages.
European Patent Office, Extended European Search Report for European Application No. 13001549.8, Jun. 18, 2013, 7 pages.
US Patent and Trademark Office, Office Action for U.S. Appl. No. 13/839,221, Mar. 12, 2015, 15 pages.
European Patent Office, Office Action for European Patent Application No. 13001549.8, Sep. 10, 2015, 6 pages.

* cited by examiner

SPECIMEN COLLECTION APPARATUS

CROSS-REFERENCE TO RELATED APPLICATIONS

This application is a divisional of U.S. patent application Ser. No. 13/839,221, which was filed on Mar. 15, 2013 and entitled "Specimen Collection Apparatus," which claims the benefit of U.S. Provisional Patent Application Ser. No. 61/615,671, which was filed on Mar. 26, 2012 and entitled "Specimen Collection Apparatus." The complete disclosures of the above applications are hereby incorporated by reference for all purposes.

FIELD OF THE DISCLOSURE

This disclosure relates to various embodiments of a specimen collection apparatus for collecting medical specimens.

BACKGROUND OF THE DISCLOSURE

Fluids are often collected for testing and/or analysis. For example, body fluids are required for diagnosis of many ailments. Often, a body fluid sample may be collected at a first location and tested at a second location spaced from the first location. For example, the diagnosis of tuberculosis and other respiratory ailments necessitates the taking of sputum samples for testing and analysis. Such specimens may be collected by a doctor, nurse, or the patient themselves in a specimen collection apparatus. The specimen collection apparatus may be transferred to a laboratory technician for testing and diagnosis.

SUMMARY OF THE DISCLOSURE

According to a first illustrative embodiment, a sample collection apparatus may include a container having an interior portion configured to contain a sample and an opening to the interior portion for receiving the sample, a funnel configured to be secured to the opening of the container (the funnel having a mouth portion and a neck portion depending from the mouth, the neck portion configured to be inserted into the opening of the container), and a closure assembly. The closure assembly may include a first closure structure configured to releasably seal the opening of the container. The first closure structure may include a chamber that is in fluid communication with the interior portion of the container when the opening is sealed by the first closure structure, and a chemical reagent contained within the chamber. The closure assembly may include a second closure structure configured to releasably cover the mouth portion of the funnel. The first closure structure may be removably attached to the second closure structure.

In a second illustrative embodiment, a sample collection assembly may include a container having an interior portion configured to contain a sample. The container may further include a first end portion having an opening to the interior portion for receiving the sample and a second end portion spaced from the first end portion. A funnel may be configured to be secured to the opening, the funnel having a mouth portion and a tapered neck portion depending from the mouth, the tapered neck portion configured to be inserted into the opening of the container. A closure assembly may include a cover configured to releasably seal the opening, the cover including a basket portion that is in fluid communication with the interior portion when the opening is sealed by the cover. A chemical reagent may be contained within the basket portion. The closure assembly may include a lid configured to releasably cover the mouth portion, the lid having a recess, the cap being configured to be removably retained in the recess. A removable seal may be configured to hermetically seal the recess and the cap retained in the recess. A base may be configured to receive the second end portion of the container to position the container, when the base is supported on a support surface, in a position at least substantially orthogonal to the support surface.

An illustrative sample collection method may include removing a lid from a mouth portion of a funnel that is removably mounted to a container. The lid may include a recess having a cap that is configured to be removably attached to an opening of the container. The cap may include an inner surface and a chamber attached to the inner surface, the chamber supporting a chemical reagent and having one or more openings. The funnel and the container with a sample deposited into an interior portion of the container may be received. The funnel may be removed from the container. The cap may be attached to the opening of the container. The sample may be exposed to the chemical reagent.

DETAILED DESCRIPTION OF THE DISCLOSURE

Figure 1:
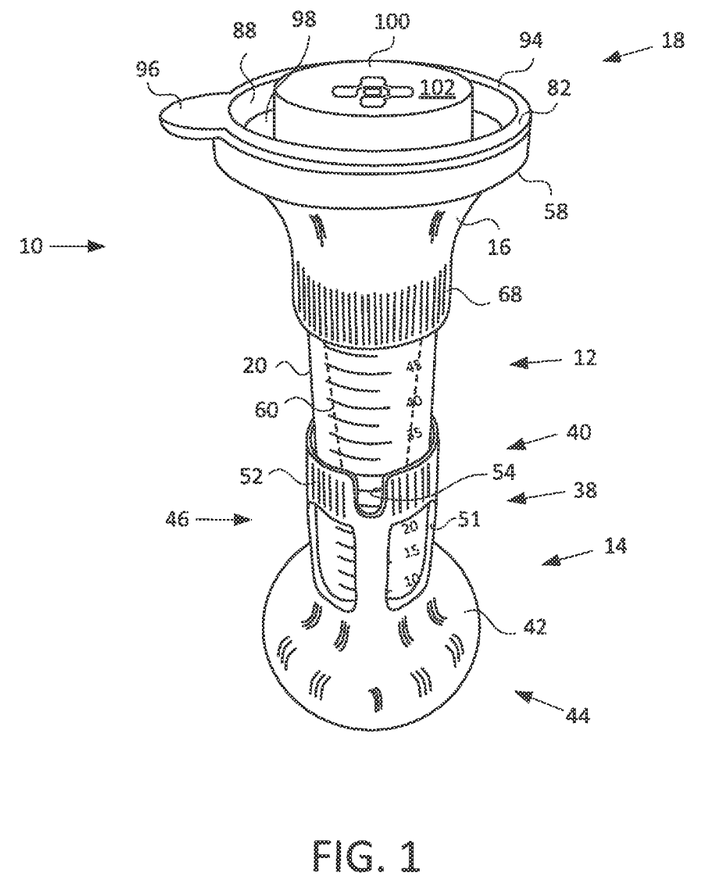
FIG. 1 shows a perspective side view of an illustrative specimen collection apparatus according to the present disclosure.
Figure 2:
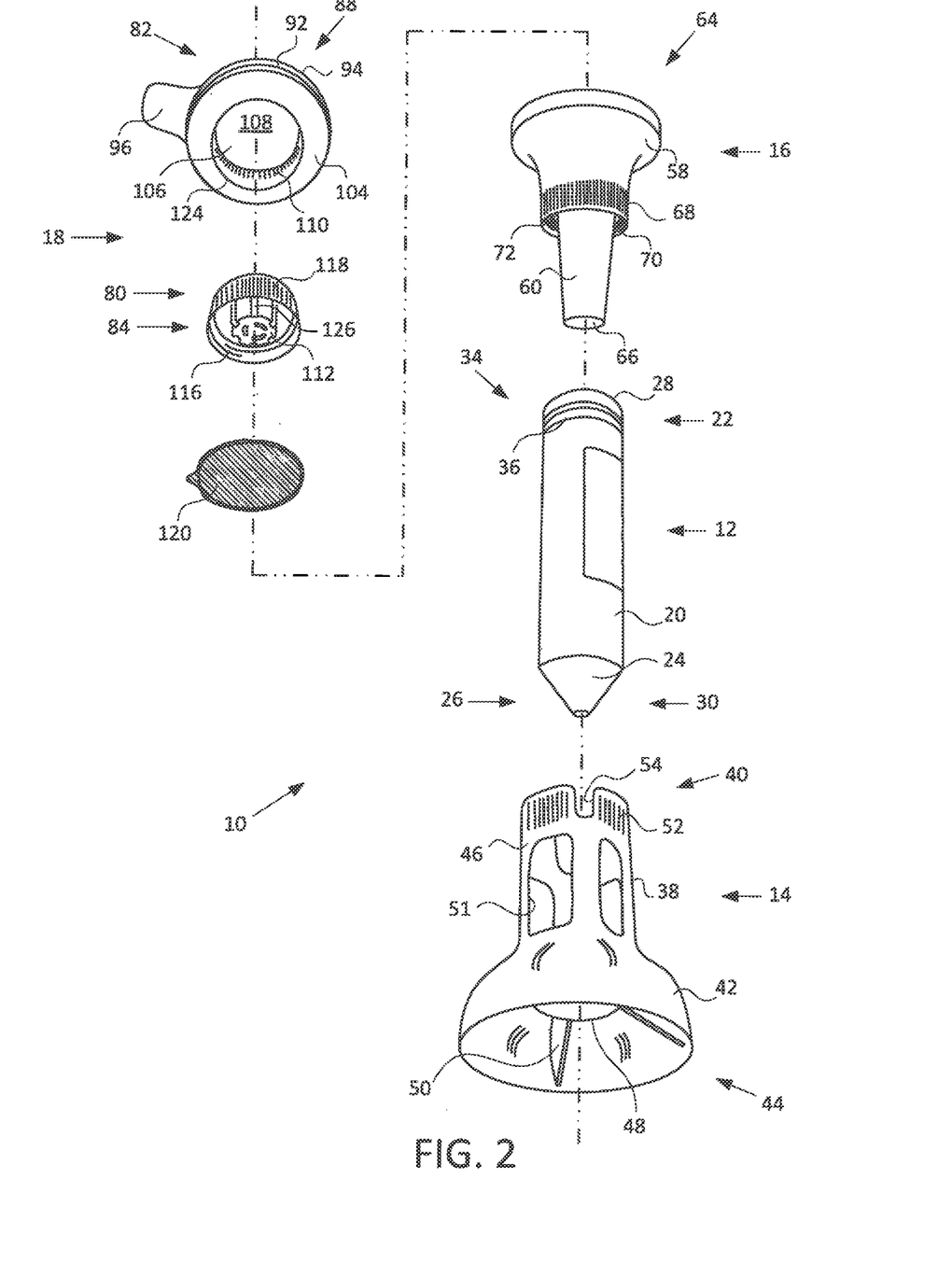
FIG. 2 shows an isometric exploded view of the apparatus of FIG. 1.
Figure 3:
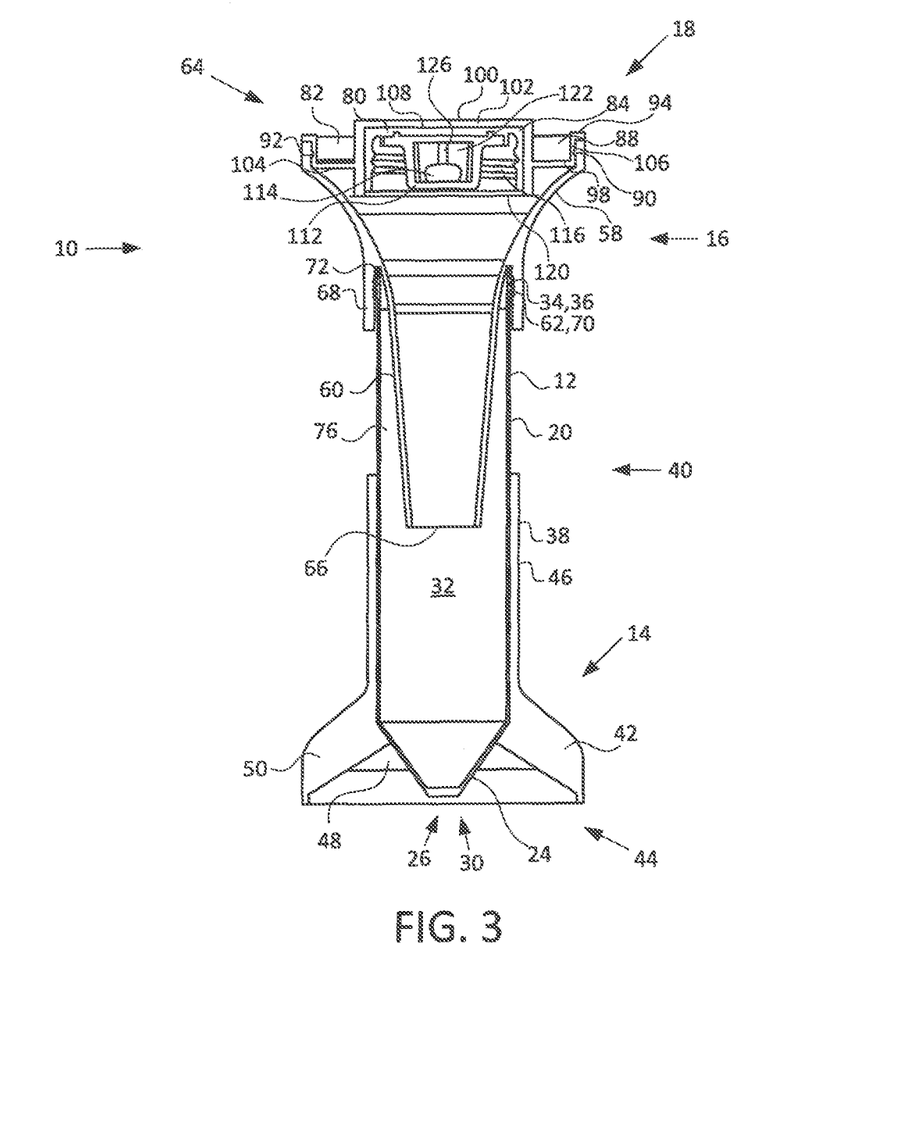
FIG. 3 is a sectional side view of the apparatus of FIG. 1.

An illustrative specimen collection apparatus is shown in FIGS. 1-3 and is generally indicated at 10. Unless explicitly stated otherwise, the specimen collection apparatus shown in FIGS. 1-3 may include one or more components and/or functions of one or more other specimen collection apparatus described in the present disclosure. Specimen collection apparatus 10 may include a specimen receptacle or container 12, a base 14, a funnel 16, and/or a closure assembly 18. Various components of apparatus 10 may be constructed of clear or colored injection molded polymers. FIG. 1 shows a perspective side view of specimen collection apparatus 10. FIG. 2 shows an isometric exploded view of apparatus 10. FIG. 3 is a sectional side view of apparatus 10.

A specimen receptacle, such as container 12, may be any suitable container for receiving and retaining a medical sample, such as a bodily fluid. For example, container 12 may include a container having an upper portion 20 at a first or upper end 22 and a lower portion 24 at a second or lower end 26, as shown in FIGS. 1-3. Upper portion 20 may be generally cylindrical with a substantially circular cross-section, and may include an opening 28. Lower portion 24 may depend from upper portion 20, may be generally conical, and/or may include a closed lower end 26. In some embodiments, upper portion 20 may have a generally rectangular cross-section, or any other suitable shape. In some embodiments, lower portion 22 may be truncated, flat, rounded, or any other suitable shape forming a lower closed end of container 12.

Together, upper portion 20 and lower portion 22 form an interior portion 28 of container 12. Receptacle or container 12 may sometimes be referred to as a "graduated test tube" or a "vial." Container 12 may be translucent and/or may be any suitable size. For example, container 12 may be one or more standard sizes used in laboratory analyses (e.g., 50 ml). Container 12 may include a closure facilitation structure 30 disposed proximate open end 24. Closure facilitation structure 30 may include any suitable structure for facilitating closure or sealing of the open end of container 12, such as with a corresponding or cooperating structure on a separate closure device. For example, as shown in FIGS. 2-3, closure facilitation structure 30 may include a container threaded portion or threads 32. In other embodiments, closure facilitation structure 30 may include a circumferentially continuous or partial flange, ridge, and/or recess.

Figure 4:
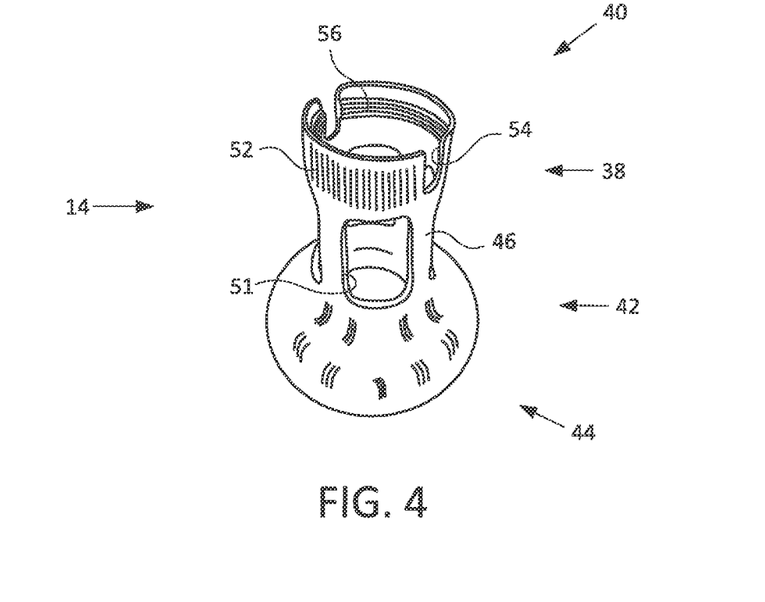
FIGS. 4 and 5 show two views of a base portion of the apparatus of FIG. 1.
Figure 5:
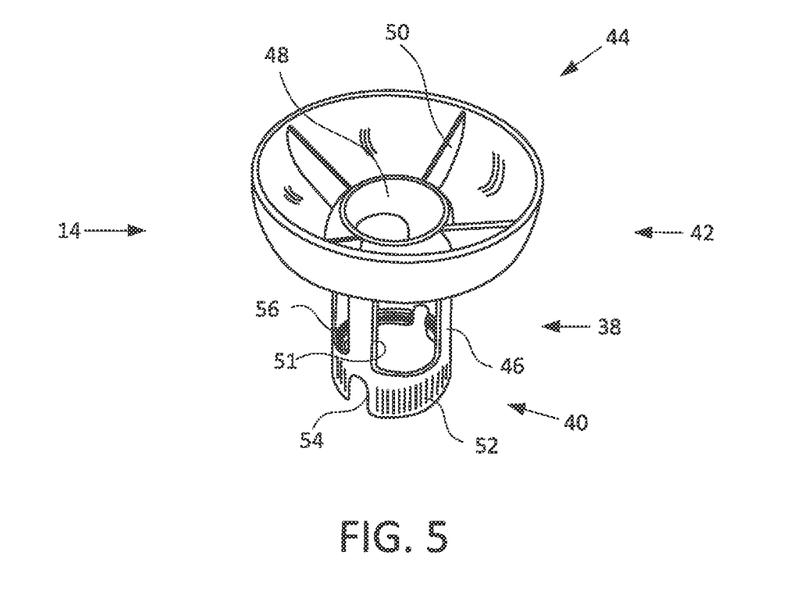

Lower end 26 of container 12 may be supported by base 14. Base 14 may include any suitable structure configured to receive and support container 12 and to generally bias the container against tipping. For example, base 14, as shown in FIGS. 1-3 and more specifically in FIGS. 4 and 5, includes a receiver portion 38 at a first end 40 and a support portion 42 at a second end 44. FIG. 4 is a perspective side view of base 14. FIG. 5 shows base 14 from a reverse perspective, showing the underside of the base. Receiver portion 38 may include a cylindrical portion 46 for receiving an inserted container, and may include a lower conical portion 48 conforming to the shape of and configured to mate with conical portion 24 of container 12. In other embodiments, lower conical portion 48 may be any other suitable shape conforming to a corresponding lower portion of the respective container. Cylindrical portion 46 may be configured for receiving and mating with cylindrical upper portion 20 of container 12. Container 12 may be removably inserted into the support portion of base 14, and base 14 may maintain container 102 in a substantially upright position. A portion of container 12 may extend beyond cylindrical portion 46.

As described above, base 14 may include support portion 42 disposed at second end 44. Support portion 42 may be disposed adjacent lower conical portion 48. Support portion 42 may be wider than container 12. For example, support portion 42 may include a perimeter, diameter, and/or circumference that is larger than a perimeter, diameter, and/or circumference of container 12, such that base 14 may support container 12 in a manner that resists tipping. Generally, base 14 may be configured to bias container 12 against tipping over when container 12 is received by receiver portion 28 and base 14 is placed on a support surface (not shown), such as a table, tray, or counter. Base 14 may be configured to support container 12 in a substantially orthogonal or orthogonal orientation relative to the support surface. Alternatively, or additionally, base 14 may be configured to support container 12 in other orientations, including one or more inclined orientations.

Base 14 may include one or more gussets 50. Gussets 50 may be any suitable structure configured to provide support to an outer surface of base 14. Gussets 50 may include substantially planar plates or fins that may be attached to an inner surface of support portion 42 as shown in FIGS. 2 and 3, and may facilitate maintenance of the shape of support portion 42 under load. Gussets 50 may be shaped to conform to conical lower portion 24 of container 12 such that the gussets may prevent container 12 from dropping or passing through base 14. Consequently, support portion 42 may include an open, closed, or partially open/partially closed lower end without compromising support of container 12.

Base 14 may include openings or apertures, such as windows 51, to facilitate viewing of an outer surface of container 12 and/or the contents of container 12 without removing container 12 from base 14. Base 14 may include one or more gripping areas 52 disposed proximate cylindrical portion 46. Gripping areas 52 may include a textured surface, such as a plurality of longitudinally disposed projections or ridges, as shown in FIGS. 1-3. Base 14 may include one or more slots 54 disposed proximate cylindrical portion 46 and/or interspersed between gripping areas 52. Gripping areas 52 and/or slots 54 may be configured such that base 14 may be gripped and compressed around container 12 or may flex outwardly to facilitate removal of container 12 from base 14. All or a portion of an inner surface 56 of cylindrical portion 46 may include a ridge or raised annular portion having a reduced diameter to increase the gripping force around container 102. In some embodiments, some or all of inner surface 56 may include a diameter substantially equivalent to an outer diameter of container 12.

Figure 6:
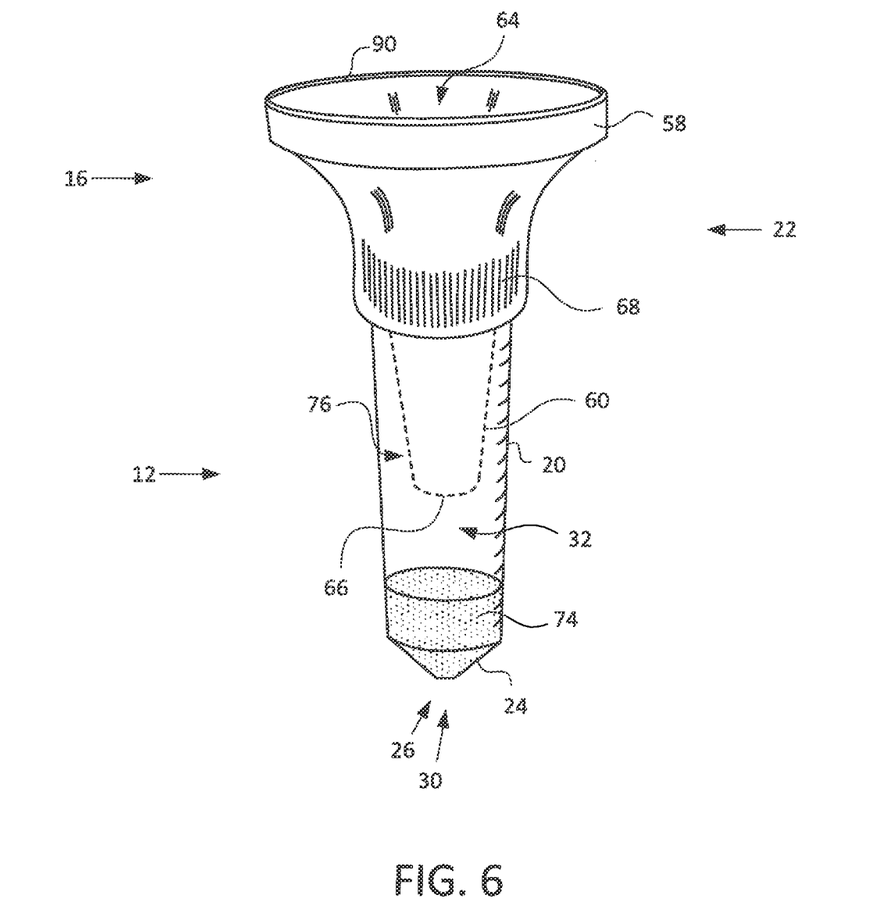
FIG. 6 shows a perspective side view of an illustrative funnel and receptacle portion of the apparatus of FIG. 1.

Specimen collection apparatus 10 may further include funnel 16, which may be removably attachable or mountable to container 12. As shown in FIG. 6, funnel 16 may be configured to be secured to opening 28 of container 12. Funnel 16 may be any suitable structure configured to facilitate and direct placement of a sample into container 12 through opening 28. For example, funnel 16 may include a mouth portion 58, a neck portion 60 depending from the mouth portion, and/or a securing element 62. Mouth portion 58 may include a large opening 64, meaning an opening having a diameter larger than the diameter of opening 28 in order to facilitate sample entry. Neck portion 60 may be a tapered or narrowed neck portion as shown in FIGS. 1-3, and more specifically in FIG. 6, and may depend from mouth portion 58. In other words, neck portion 60 may extend from mouth portion 58, in a direction away from large opening 64 toward a smaller opening 66 at an end opposite the large opening. For example, smaller opening 66 may have a diameter smaller than opening 28. Neck portion 60 may be configured to be inserted into opening 28, thereby extending into the interior portion of container 12.

Securing element 62 may be any suitable structure or device configured to allow removable attachment of funnel 16 to container 12. For example, securing element 62 may include a threaded flange or skirt portion 68 extending from an exterior surface of mouth portion 58. An exterior surface of securing element 62 may be ribbed and/or otherwise textured to facilitate removable attachment to the upper portion of container 12. Securing element 62 may include a structure for mating or otherwise attaching to closure facilitation structure 34 of container 12. For example, an inside surface of securing element 62 may include a funnel threaded portion (such as threads 70), which may engage with threads 36 of container 12 and force container 12 into a funnel sealing surface 72. In other words, closure facilitation structure 34 and securing element 62 may include complementary threaded portions. Such sealing of opening 28 of container 12 prevents accidental specimen leakage and/or contamination of the operator or outside of container 102. In other embodiments, securing element 62 may include a ridge, clamping structure, or tab for engaging with a corresponding element of closure facilitation structure 34. In some embodiments, funnel 16 may snugly and securely seal onto opening 28 with a friction fit.

Funnel 16 may be configured such that, should the specimen collection apparatus be tipped on a side during use, or even inverted, a specimen 74 located in interior portion 32 of container 12 will be substantially prevented from spilling out of opening 28 and/or large opening 64 of funnel 16. For example, neck portion 60 may extend from sealing surface 72 to the discharge end at small opening 66, extending substantially into container 12. Small opening 66 may include a diameter, perimeter, and/or circumference that is less than a diameter, perimeter, and/or circumference of container 12. Because the container may contain a pH buffered solution, funnel 16 may be configured to keep the solution from flowing out of the container, into the funnel, and up to the lid (if present). This may be accomplished by having the funnel extend into the container far enough and tapered to allow the specimen collection apparatus to lay on its side without having the sample flow outside of the container.

As best shown in FIG. 6, neck portion 60 may be elongated and tapered such that, when funnel 16 is secured to opening 28, a volumetric space 76 is defined and created between an outer surface of neck portion 60 and an inner surface or wall of container 12. The neck portion may have any suitable length and/or any suitable taper. For example, neck portion 60 may extend into interior portion 32 such that opening 66 is located at approximately or about the half-way point of the axial length of container 12. Additionally, neck portion 60 may taper such that the diameter of funnel 16 at opening 66 is approximately or about half of the inner diameter of container 12. As such, if container 12 is supported on a support surface in a generally horizontal position or beyond, such as if container 12 is inverted, a predetermined volume of the sample may be retained within the container between the neck portion and the inner wall of the container. For example, volumetric space 76 may define a volume "V" that is a certain percentage of an overall volume of interior portion 32 of container 12. In some embodiments, "V" may be greater than or equal to approximately 10% of the overall volume of container 12. Accordingly, if specimen collection apparatus 10 is tipped over, specimen 74, or a portion thereof, may be trapped between the inside surface of container 12 and the outside surface of funnel 16.

Mouth portion 58 of funnel 16 may include a diameter, perimeter, and/or circumference that is greater than or equal to a diameter, perimeter, and/or circumference of base 14. Accordingly, should specimen collection apparatus 10 be tipped on a side, opening 28 may be propped up at the same height or higher than closed end 30, when funnel 16 is attached to container 12.

Figures 7, 8, 9, 10:
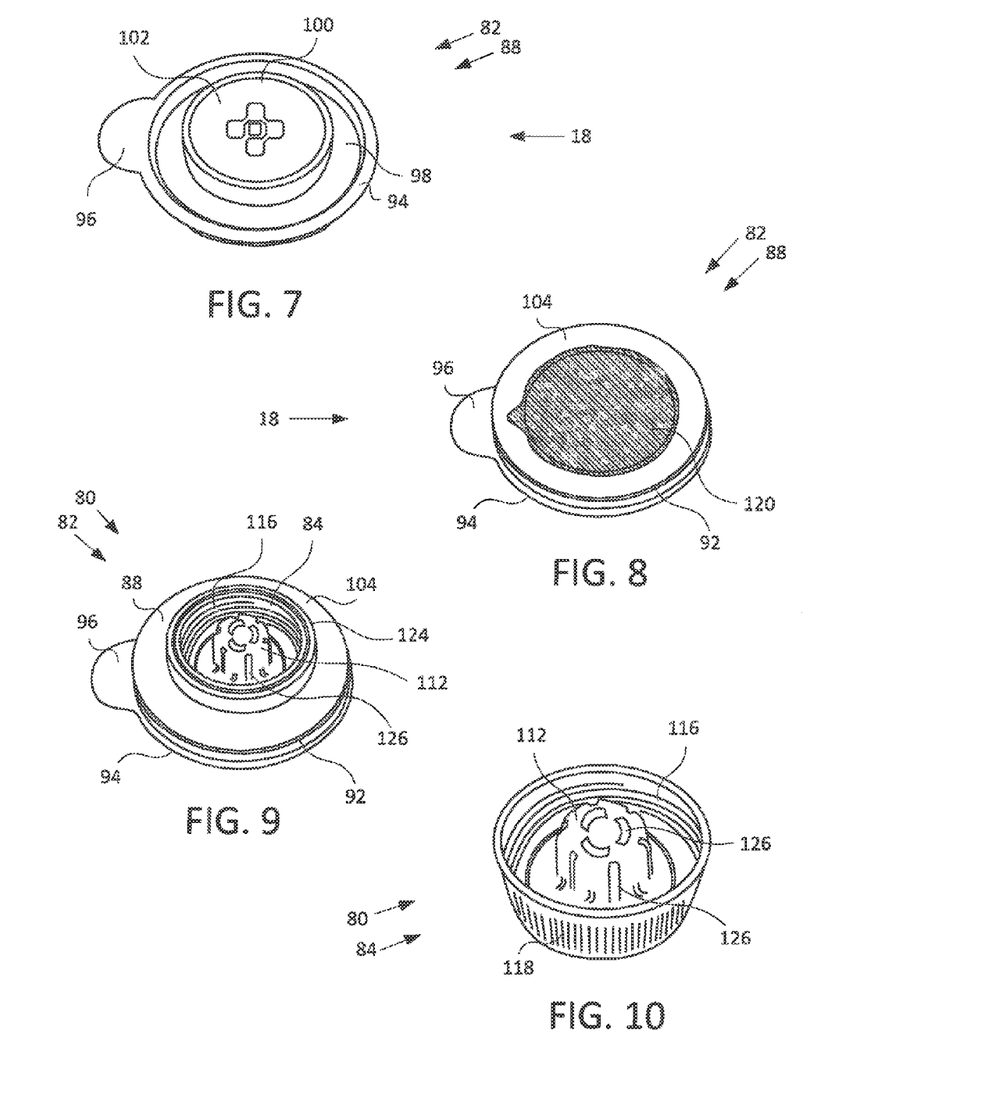
FIG. 7 shows an overhead perspective view of a closure assembly or lid of the apparatus of FIG. 1.
FIG. 8 shows a bottom perspective view of the assembly of FIG. 7.
FIG. 9 shows a perspective view of an illustrative lid and attached cap of the assembly of FIG. 7.
FIG. 10 shows a perspective view of an illustrative cap of the assembly of FIG. 7.

Closure assembly 18 may include a first closure structure 80 and a second closure structure 82, as shown in FIGS. 1-3 and more specifically in the various views of FIGS. 7-10. FIG. 7 shows closure assembly 18 in a top perspective view. FIG. 8 shows a reverse perspective, revealing the underside of the closure assembly. FIG. 9 shows the first and second closure structures nested or removably connected to each other. FIG. 10 shows a detained perspective view of the first closure structure.

First closure structure 80 may include any suitable structure configured to releasably seal opening 28 of container 12. For example first closure structure 80 may include a cover or cap 84. Second closure structure 82 may include any suitable structure configured to cover, seal, or close opening 64 of mouth portion 58 of the funnel. For example, second closure structure 82 may include a funnel lid 88. First closure structure 80 may be releasably or removably attached to second closure structure 82. For example, cap 84 may be friction fit into a recess of lid 88 as further described below.

Mouth portion 58 may be removably sealed or covered by funnel lid 88 during use and/or when the apparatus is in a storage location (see FIG. 1). An inside perimeter surface of mouth portion 58 may include a mouth ridge 90. Funnel lid 88 may include a resiliently compressible lid ridge 92 that may be positionable on the underside of mouth ridge 90, thereby securing lid 88 onto mouth portion 58 and substantially covering the opening. Lid 88 may further include a lip 94 around the perimeter of lid 88 that may rest over and/or seal the periphery of opening 64. Lid 88 may further include a tab 96 for grasping and/or removal of lid 88. Funnel lid 148 may include a diameter, perimeter, and/or circumference that is greater than or equal to a diameter, perimeter, and/or circumference of support portion 42 of base 14, such that, should the specimen collection apparatus be tipped on a side during use, opening 28 may be propped up at the same height or higher than closed end 30, when funnel 16 and lid 88 are attached to container 12.

As noted above, funnel lid 88 may enclose specimen 74 within container 12 and/or bar any outside elements from entering container 12 during use or storage. An upper surface 98 of lid 88 may include a central portion 100 that may be raised above the surrounding upper surface, as shown in FIG. 7. Central portion 100 may include a roof 102 having an outside surface that is relatively planar. A lower surface 104 of lid 88 may include a cavity or recess 106 extending into central portion 100. Recess 106 may include a ceiling 108 that is relatively planar and disposed opposite roof 102. Recess 106 may be configured to conform to an outer shape and size of cap 84, and may include a textured surface 110, such as ridges or ribs, around at least a portion of the periphery of the recess. In other words, the inner surface that forms recess 106 may include a number of radially extending projections or other texturing, spaced about the periphery of recess 106 to provide a friction fit with a corresponding textured surface on cap 84.

As described above, first closure structure 80 may include a cap 84 as shown in FIGS. 9 and 10. First closure structure 80 and cap 84 may be referred to interchangeably, and may also be referred to herein as a "dispensing assembly" because the cap may be configured to dispense one or more chemical reagents into container 12 during use. Accordingly, the dispensing assembly or first closure structure 80 may further include a reagent housing 112 and/or a chemical reagent 114 (also referred to as "reagent" or "agent").

Cap 84 may include a cap threaded portion 116 configured to be complementary to a container threaded portion, such as threads 36. In other words, the inside periphery of cap 84 may include threads for releasable attachment to container threads 36 such that container 12 may be releasably sealed by cap 84.

A lateral external surface 118 of cap 84 may include ribs, ridges, and/or other textured surface to facilitate manual gripping and to interface with surface 110 of lid 88. Cap 84 may be disposed centrally within recess 106 of lid 88 and may be peripherally gripped therein. Specifically, cap 84 may fit within the space defined by textured surface 110. An exterior surface of cap 84 may be disposed against ceiling 108 and/or an inside surface of cap 84 may face away from ceiling 108.

Closure assembly 18 of specimen collection apparatus 10 may further include a removable hermetic seal 120 as shown in FIGS. 2 and 8. Removable seal 120 may include any suitable structure configured to prevent accidental reagent leakage and/or contamination of the reagent by hermetically sealing the chemical reagent within closure assembly 18. For example, removable seal 120 may include a foil and/or plastic liner or sheet. Additionally and/or alternatively, removable seal 120 may serve as a gas barrier to create an atmosphere 122 having a different composition than the composition of surrounding air. In some embodiments, atmosphere 122 may be a nitrogen purged atmosphere. Atmosphere 122 may be a reagent-specific atmosphere, and/or may be configured to preserve the reagent or hold the reagent in an inert status until desired use. Removable seal 120 may also prevent cap 84 from falling out of lid 88 during handling.

In some embodiments, removable seal 120 may seal first closure structure 80 (including cap 84, reagent housing 112, and reagent 114) within recess 106 of lid 88. For example, a lower periphery 124 of lid 88 and/or recess 106 may extend beyond first closure structure 80 when closure structure 80 is retained within recess 106. Removable seal 120 may be attached to lower periphery 124 such that first closure structure 80 may be sealed inside recess 106 during use of specimen collection apparatus 10, but prior to the need for reagent 114 to be dispensed into container 12 and/or specimen 74. As described above, removable seal 120 may further provide a barrier to prevent first closure structure 80 from accidentally falling or otherwise moving out of recess 106. In some embodiments, removable seal 120 may be a degradable seal, such as a seal that degrades following (or in response to) addition of the sample to container 12.

In other embodiments, a removable seal, such as seal 120, may be attached to first closure structure 80 to prevent accidental reagent leakage and/or contamination or other adverse effects on the reagent. For example, a removable seal (not shown) may be attached directly to a lower periphery of cap 84 such that the reagent housing, reagent specific atmosphere and/or reagent are sealed within cap 84. Removable seal 120 may be attached to whatever the desired surface by ultrasonic welding, adhesive, or any other suitable means.

Reagent housing 112 may be any suitable structure operatively attached to and disposed within first closure structure 80, and configured to releasably contain or retain reagent 114. Specifically, reagent housing 112 may include a chamber configured to be in fluid communication with the interior portion of container 12 when opening 28 is sealed by the first closure structure 80. Reagent housing 112 may include a structure herein referred to as a "basket," a "cage," or a "chamber." Reagent housing 112 may be disposed, attached, and/or hermetically sealed adjacent an inside surface of cap 84 for releasably retaining reagent 114, such as a dissolvable tablet. Although the following description refers to a reagent housing for retaining a reagent including a dissolvable tablet or tablets, reagent 114 may include one or more of granule(s), liquid(s), tablet(s), capsule(s), chemical reagent coating(s), etc. The reagent may be dissolvable or non-dissolvable. Additionally, the reagent may be any suitable size(s) and/or amount(s). Moreover, the reagent may contain from one chemical to several chemicals to complete any required reaction(s).

Reagent housing 112 may extend from an inside surface of cap 84. The housing may be rigid or semi-rigid, and may be held to the cap using glue or other joining method, such as ultrasonic welding. Any suitable joining method capable of withstanding forces experienced during, for example, sample centrifugation may be used. The reagent housing may include a cage or basket-shaped structure including one or more apertures 126 radially extending along the lateral periphery and/or one or more apertures 126 disposed at the bottom surface of the housing. Apertures 126 may be smaller than reagent 114 (such as when reagent 114 is a dissolvable tablet) and/or may be sized to allow an influx and outflux of adjacent specimen 74. During use, some or all of specimen 74 may pass in and out of reagent housing 112 to dissolve reagent 114. In other examples, reagent 114 may be described as passing through the apertures to communicate or mix with the specimen.

Reagent 114 may include multiple reagents or chemicals in compressed tablet form (or chemical reagent coating(s), granule(s), capsule(s), etc.) and/or may include one or more of the following components: a mucolytic agent used to disrupt disulfide bonds, a chelating component used to sequester inhibitory ions, a pH altering reagent(s) to achieve and maintain neutrality of the specimen during transport to the laboratory, and/or necessary excipients for tablet formulation and stability. For example, some embodiments of reagent 114 may include a homogenization agent, such as for sputum (e.g., in tablet form). The homogenization agent may include one or more of a mucolytic compound, a chelating component, a pH altering reagent and/or an excipient. The homogenization agent may, for example, be used as a pretreatment for sputum in a method of detecting a microbe (or microbes).

The mucolytic compound may include guaifenesin, N-acetyl-L-cysteine, dithiothreitol, and/or other suitable mucolytic compound(s). The chelating component may include ethylenediaminetetraacetic acid, ethylene glycol tetraacetic acid, trisodium citrate, nitrilotriacetic acid, and/or other suitable chelating component(s). The pH altering reagents may include hydrochloric acid, sodium hydroxide, potassium hydroxide, dipotassium phosphate, monopotassium phosphate, sodium carbonate, and/or other suitable pH altering reagent(s). Additionally and/or alternatively, the pH altering reagent may render a final pH of a patient specimen to be neutral and/or between a pH of about 6.9 to a pH of about 8.1. The excipient may include sucrose, lactose, xylitol, amylose, amylopectin, cellulose, sodium starch glycolate, hydroxypropyl methylcellulose, gelatin, and/or any other suitable excipient(s).

Figure 11:
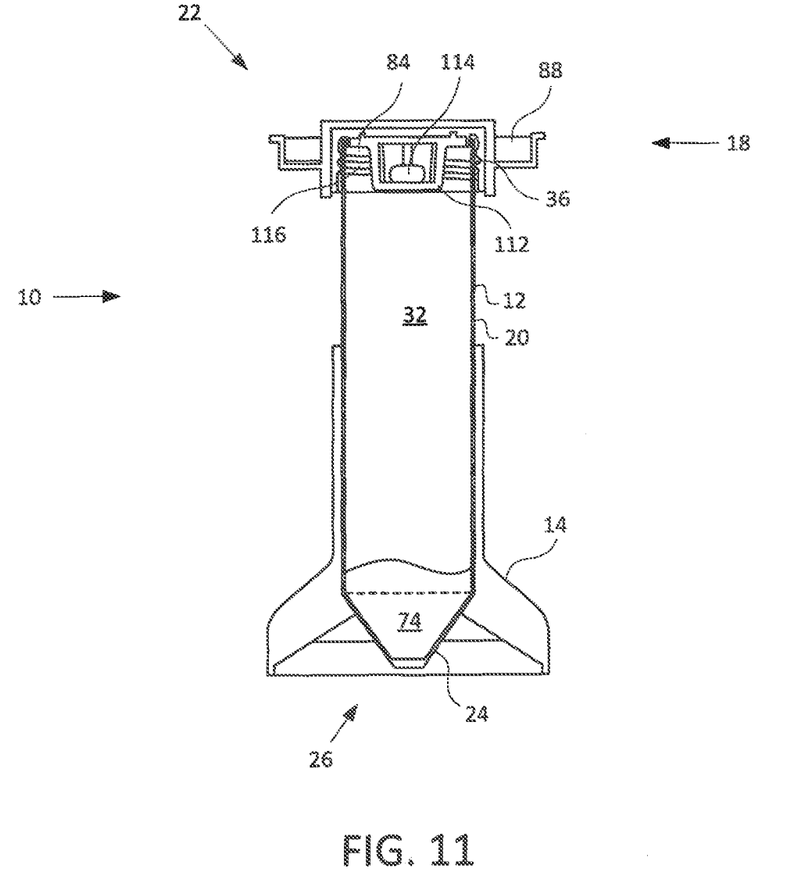
FIG. 11 is a sectional side view of the apparatus of FIG. 1 with a funnel portion removed and a closure assembly sealed to a container portion.

Turning to FIG. 11, a sectional side view of specimen collection apparatus 10 is shown. In this arrangement of the apparatus, funnel 16 has been removed from container 12, which contains sample or specimen 74. Closure assembly 18 has been attached to opening 28 by threading cap 84 onto upper end 22. As shown in the drawing, lid 88 remains attached to cap 84. Lid 88 may be manually rotated to thread cap 84 onto container 12 because textured surfaces 110 and 118 interact to substantially prevent the lid and cap from rotating relative to each other, while still allowing manual removal of lid 88 from cap 84 using axial and/or oblique force. Removable seal 120 has also been removed to allow both attachment of the cap and fluid communication between the interior portion of container 12 and the interior of reagent housing 112. Reagent 114 is located within housing 112.

Figure 12:
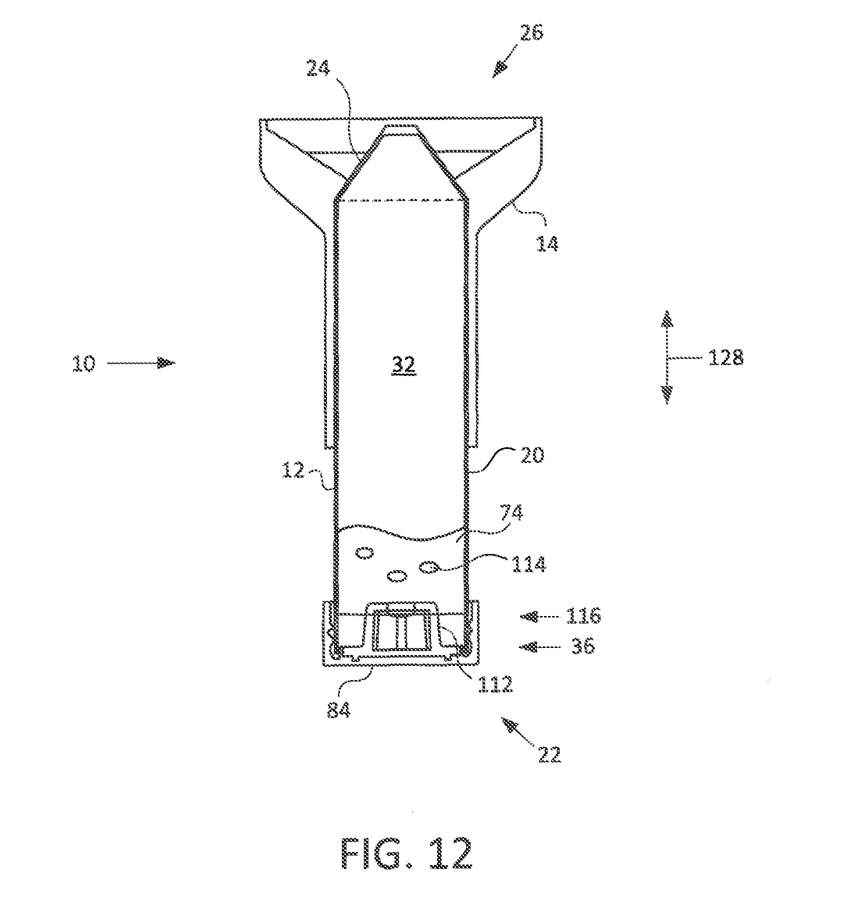
FIG. 12 is a sectional side view of an inverted apparatus of FIG. 1 with the funnel and lid removed and a cap sealing the container portion.

FIG. 12 shows a sectional side view of the apparatus of FIG. 11 in which lid 88 has been removed and the apparatus has been inverted, bringing specimen 74 and reagent 114 into physical contact with each other through apertures 126 in the reagent housing. Arrows 128 indicate that the apparatus may be manipulated by shaking or moving the apparatus back and forth in a substantially axial direction to facilitate or enhance mixing and/or reaction of specimen 74 and reagent 114. As depicted in FIG. 12, reagent 114 may dissolve or otherwise disperse into specimen 74.

Figure 13:
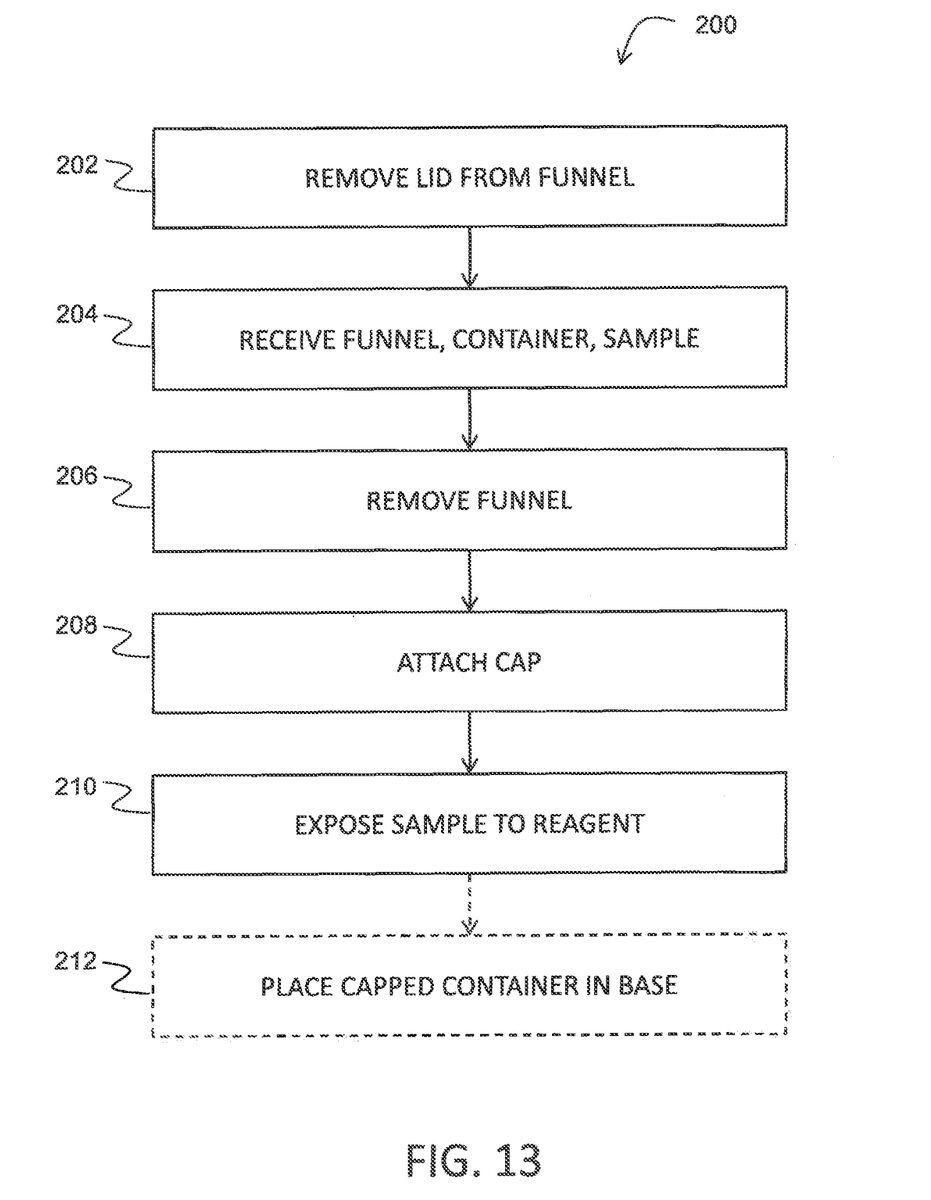
FIG. 13 is a block diagram of an illustrative sample collection method.

FIG. 13 is a block diagram of an illustrative method 200 for using specimen collection apparatus 10 to collect a biological or other sample. Step 202 of method 200 may include removing lid 88 from mouth portion 58 of funnel 16, where the funnel is mounted to container 12 and cap 84 is attached to the lid, with the cap containing reagent 114 disposed in housing 112 as described above. Removal of the lid may include manually grasping tab 96 and prying, pulling, urging, and/or otherwise applying force to the lid to remove the lid from funnel 16. Closure assembly 18, including lid 88 and cap 84, may be placed aside for use in following steps.

Step 204 of method 200 may include receiving funnel 16 and container 12 with a sample or specimen deposited into interior portion 32 of the container. The sample or specimen may be deposited by a laboratory technician, a doctor or nurse, and/or a patient or donor, and may be deposited into interior portion 32 through funnel 16. In some examples, the container may include a small volume of collection fluid prior to deposit of the sample. The collection fluid may include sterile buffered water that mixes with the deposited sample and may aid in the dissolution of the reagent tablet(s).

Lid 88 may be placed atop funnel 16 by the person depositing the sample, or the lid may be attached after it is received, in order to prevent contamination of the sample in transit or storage before further steps are undertaken. At this step, the dispensing assembly may or may not be attached to the lid, depending on a preference of the user or the specific testing regime.

Step 206 of method 200 may include removing funnel 16 from container 12. For example, funnel 16 may be grasped by mouth portion 58 or more preferably by skirt portion 68 of securing element 62, and unscrewed, unthreaded, and/or unclamped from container 12. Neck portion 60 may be removed from interior portion 32 through opening 28. Funnel 16 may be placed aside or disposed of in any suitable manner.

Step 208 of method 200 may include attaching cap 84 to opening 28 of container 12. For example, closure assembly 18 may be threaded onto container 12 by placing first closure structure 80 onto opening 28 and manually rotating second closure structure 82 clockwise. This method allows cap 84 to be attached to opening 28 without a user needing to place his or her fingers near or on the cap or opening. Optionally, lid 88 may then be removed from cap 84 by manually prying or otherwise applying axial and/or oblique force to the lid while holding the cap or cap and container substantially stationary. In some examples of method 200, cap 84 and lid 88 may be separated before attaching cap 84 to container 12. Attaching cap 84 to opening 28 may include removing hermetic seal 120 covering the cap by peeling, cutting, tearing, and/or otherwise separating the seal from the closure assembly.

Step 210 of method 200 may include exposing the sample to chemical reagent 114. For example, attaching cap 84 to container 12 may expose the chemical to the interior of container 12, and may be sufficient to expose the sample or specimen. In other examples, the sample and the chemical reagent may be caused to come into physical contact by manipulating the container. For example, the capped container may be inverted to cause the sample to fall into the interior portion of the cap, and accordingly into direct contact with the reagent. In other examples, the capped container may also or instead be shaken or agitated such that the sample comes into repeated and/or active contact with the reagent. Once the reagent is dissolved, the apparatus may be turned right side up (if previously inverted). The liquefied specimen, reagents, and apparatus may then be transported to the laboratory and used to perform diagnostic tests and/or prepare the sample for further processing. Upon receipt in the laboratory, the specimen may be centrifuged while in collection container 12. Once processed, the tablet and collection solution reagents may be configured not to interfere with subsequent diagnostic tests, specifically those utilizing polymerase chain reaction and transcription-mediated amplification technologies.

Step 212 may include placing the capped container into base 14. As described above, base 14 may thereby support the container in a position orthogonal to the support surface on which the base is sitting. In other examples, container 12 may be placed in base 14 during or before a previous step, or may remain in base 14 throughout the method. In some examples, the capped container may instead be accommodated by a test tube rack or similar device until it is needed for centrifuging and/or testing. Capped container 12 and base 14 may be placed on a hospital cart or other suitable apparatus for transport or into a refrigerator or other storage area. The relatively low center of gravity and greater width of base 14 resists tipping, as described above. Other embodiments of method 200 may add, omit, and/or modify one or more of the above steps.

Some embodiments of the disclosure may be described as a biological specimen device (or sputum collection device) that contains tablet(s) and liquids utilized in the collection device and designed to liquefy the specimen, stabilize the pH of the liquefied specimen, and be compatible with diagnostic procedures (such as microbial cultures, diagnostic stains, bacterial growth retention [within 48 hours], PCR and TMA procedures, where PCR means polymerase chain reaction and TMA means transcription-mediated amplification or Mass Spectrometry).

Some embodiments of the disclosure may be described as a biological specimen apparatus (or sputum collection apparatus) that positions reagent tablet(s) in the specimen cap, ultrasonically sealed so that the cap can be subjected to centrifugation, in the laboratory, at speeds up to 3,200×g's.

Some embodiments of the disclosure may be described as a biological specimen apparatus (or sputum collection apparatus) that retains the chemical stability and activity of the tablet(s) in a cap design where the ambient air is replaced with a heavier inert gas and sealed within the lid of the funnel. The funnel lid houses the specimen cap, housing a ultrasonically sealed grid which contains the tablet(s) utilizing matching offsetting grooves so that the cap will not fall out and the cap can be screwed onto the specimen tube without touching the top of the specimen vial, removing a potential contamination point.

Based on the above description and the associated drawings, the following examples describe various embodiments of apparatuses and methods of the disclosure.

In a first example, a sample collection apparatus may include a container having an interior portion configured to contain a sample and an opening to the interior portion for receiving the sample, a funnel configured to be secured to the opening of the container (the funnel having a mouth portion and a neck portion depending from the mouth, the neck portion configured to be inserted into the opening of the container), and a closure assembly. The closure assembly may include a first closure structure configured to releasably seal the opening of the container. The first closure structure may include a chamber that is in fluid communication with the interior portion of the container when the opening is sealed by the first closure structure, and a chemical reagent contained within the chamber. The closure assembly may include a second closure structure configured to releasably cover the mouth portion of the funnel. The first closure structure may be removably attached to the second closure structure.

The sample collection apparatus may include a removable seal configured to hermetically seal the chemical reagent within the closure assembly.

The neck portion may be elongated and tapered such that, when the funnel is secured to the opening and the container is supported on a support surface in a generally horizontal position, a predetermined volume of the sample is retained within the container between the neck portion and an inner wall of the container.

The first closure structure may include a cap and the second closure structure may include a lid.

The chamber may be mounted to an inner surface of the cap.

The chamber may include a plurality of openings such that an inner portion of the chamber is in fluid communication with the interior portion of the container.

The lid may include a recess and the cap may be configured to be removably retained in the recess.

A removable seal may be configured to hermetically seal the recess with the cap retained in the recess.

The container may include a container threaded portion adjacent the opening, and the cap may include a cap threaded portion complementary to the container threaded portion.

The mouth portion may include a mouth threaded portion that is complementary with the container threaded portion.

The sample collection apparatus may include a base having first and second ends, the first end including a receiver portion that is configured to receive a portion of the container, the second end including a support portion configured to bias the container against tipping over when the container is received by the receiver portion and the base is placed on a support surface.

In a second example, a sample collection assembly may include a container having an interior portion configured to contain a sample. The container may further include a first end portion having an opening to the interior portion for receiving the sample and a second end portion spaced from the first end portion. A funnel may be configured to be secured to the opening, the funnel having a mouth portion and a tapered neck portion depending from the mouth, the tapered neck portion configured to be inserted into the opening of the container. A closure assembly may include a cover configured to releasably seal the opening, the cover including a basket portion that is in fluid communication with the interior portion when the opening is sealed by the cover. A chemical reagent may be contained within the basket portion. The closure assembly may include a lid configured to releasably cover the mouth portion, the lid having a recess, the cap being configured to be removably retained in the recess. A removable seal may be configured to hermetically seal the recess and the cap retained in the recess. A base may be configured to receive the second end portion of the container to position the container, when the base is supported on a support surface, in a position at least substantially orthogonal to the support surface.

The base may include a plurality of apertures.

An illustrative sample collection method may include removing a lid from a mouth portion of a funnel that is removably mounted to a container. The lid may include a recess having a cap that is configured to be removably attached to an opening of the container. The cap may include an inner surface and a chamber attached to the inner surface, the chamber supporting a chemical reagent and having a plurality of openings. The funnel and the container with a sample deposited into an interior portion of the container may be received. The funnel may be removed from the container. The cap may be attached to the opening of the container. The sample may be exposed to the chemical reagent.

Attaching the cap to the opening of the container may include removing a hermetic seal covering the cap.

Attaching the cap to the opening of the container may include attaching the cap to the opening of the container while in the recess of the lid and removing the lid from the attached cap.

Exposing the sample to the chemical reagent may include manipulating the receptacle to cause the sample and the chemical reagent to come into physical contact with each other.

Manipulating the receptacle to cause the sample and the chemical reagent to come into physical contact with each other may include inverting the container to bring the sample and the chemical reagent in physical contact with each other.

Manipulating the receptacle to cause the sample and the chemical reagent to come into physical contact with each other may include shaking the container to bring the sample and the chemical reagent in physical contact with each other.

The capped container may be placed in a base that supports the container in a position orthogonal to a support surface when the base is placed on the support surface.

Numbered paragraphs that describe further examples of suitable reagents are provided below.

1. A homogenization agent for sputum in tablet form, comprising of one or more of the following:
   a. Mucolytic compounds;
   b. Chelating components;
   c. pH altering reagents; and
   d. Excipients 2. The homogenization agent according to paragraph 1, wherein the mucolytic compound is at least one member selected from the group consisting of guaifenesin, N-acetyl-L-cysteine, and dithiothreitol.

3. The homogenization agent according to paragraph 1, wherein the chelating component is at least one member selected from the group consisting of ethylenediaminetetraacetic acid, ethylene glycol tetraacetic acid, trisodium citrate, and nitrilotriacetic acid.

4. The homogenization agent according to paragraph 1, wherein the pH altering reagents are at least one member selected from the group consisting of hydrochloric acid, sodium hydroxide, potassium hydroxide, dipotassium phosphate, monopotassium phosphate, and sodium carbonate.

5. The homogenization agent according to paragraph 1, wherein the pH altering reagents will render the final pH of the patient specimen to be neutral, between pH 6.9 and 8.1.

6. The homogenization agent according to paragraph 1, wherein the excipients are at least one member selected from the group consisting of sucrose, lactose, xylitol, amylose, amylopectin, cellulose, sodium starch glycolate, hydroxypropyl methylcellulose, and gelatin.

7. The homogenization agent according to paragraph 1, wherein the homogenization agent is used as a pretreatment for sputum in a method of detecting a microbe or microbes.

It is believed that the disclosure set forth herein encompasses multiple distinct inventions with independent utility. While each of these inventions has been disclosed in its preferred form, the specific embodiments thereof as disclosed and illustrated herein are not to be considered in a limiting sense as numerous variations are possible. Each example defines an embodiment disclosed in the foregoing disclosure, but any one example does not necessarily encompass all features or combinations that may be eventually claimed.

Where the description recites "a" or "a first" element or the equivalent thereof, such description includes one or more such elements, neither requiring nor excluding two or more such elements. Further, ordinal indicators, such as first, second or third, for identified elements are used to distinguish between the elements, and do not indicate a required or limited number of such elements, and do not indicate a particular position or order of such elements unless otherwise specifically stated.

What is claimed is:

1. A sample collection method, comprising:
    removing a lid from a mouth portion of a funnel, the funnel removably mounted to a container, the lid including a recess having a cap that is configured to be removably attached to an opening of the container, the cap including an inner surface and a chamber attached to the inner surface, the chamber supporting a chemical reagent and having one or more openings;
    receiving a sample through the funnel and into an interior portion of the container;
    removing the funnel from the container;
    attaching the cap to the opening of the container; and
    exposing the sample in the interior portion of the container to the chemical reagent.

2. The method of claim 1, wherein attaching the cap to the opening of the container includes removing a hermetic seal covering the cap.

3. The method of claim 1, wherein attaching the cap to the opening of the container includes attaching the cap to the opening of the container while in the recess of the lid and removing the lid from the attached cap.

4. The method of claim 1, wherein exposing the sample in the interior portion of the container to the chemical reagent includes manipulating the container to cause the sample in the interior portion of the container and the chemical reagent to come into physical contact with each other.

5. The method of claim 4, wherein manipulating the container to cause the sample in the interior portion of the container and the chemical reagent to come into physical contact with each other includes inverting the container to bring the sample in the interior portion of the container and the chemical reagent in physical contact with each other.

6. The method of claim 4, wherein manipulating the receptacle to cause the sample and the chemical reagent to come into physical contact with each other includes shaking the container to bring the sample and the chemical reagent in physical contact with each other.

7. The method of claim 1, further comprising placing the capped container in a base that supports the container in a position orthogonal to a support surface when the base is placed on the support surface.

* * * * *